US011666083B2

(12) United States Patent
Cantrell et al.

(10) Patent No.: US 11,666,083 B2
(45) Date of Patent: *Jun. 6, 2023

(54) MELTABLE SMOKELESS TOBACCO COMPOSITION

(71) Applicant: R.J. REYNOLDS TOBACCO COMPANY, Winston-Salem, NC (US)

(72) Inventors: Daniel Verdin Cantrell, Lewisville, NC (US); Gong Chen, Clemmons, NC (US); Matthew William Benford, Winston-Salem, NC (US); Thaddeus Jude Jackson, High Point, NC (US)

(73) Assignee: R.J. Reynolds Tobacco Company, Winston-Salem, NC (US)

( * ) Notice: Subject to any disclaimer, the term of this patent is extended or adjusted under 35 U.S.C. 154(b) by 18 days.

This patent is subject to a terminal disclaimer.

(21) Appl. No.: 16/992,822

(22) Filed: Aug. 13, 2020

(65) Prior Publication Data

US 2020/0367551 A1 Nov. 26, 2020

Related U.S. Application Data

(63) Continuation of application No. 15/988,004, filed on May 24, 2018, now Pat. No. 10,772,350, which is a continuation of application No. 14/868,867, filed on Sep. 29, 2015, now Pat. No. 9,993,020, which is a continuation of application No. 13/330,929, filed on Dec. 20, 2011, now Pat. No. 9,155,321, which is a continuation-in-part of application No. 12/854,342, filed on Aug. 11, 2010, now Pat. No. 11,116,237.

(51) Int. Cl.
| | |
|---|---|
| *A24B 15/30* | (2006.01) |
| *A61K 9/00* | (2006.01) |
| *A23G 1/36* | (2006.01) |
| *A23G 1/48* | (2006.01) |
| *A23G 3/48* | (2006.01) |
| *A23G 3/40* | (2006.01) |
| *A23G 4/06* | (2006.01) |
| *A24B 13/00* | (2006.01) |
| *A24B 15/24* | (2006.01) |

(52) U.S. Cl.
CPC .............. *A24B 15/303* (2013.01); *A23G 1/36* (2013.01); *A23G 1/48* (2013.01); *A23G 3/40* (2013.01); *A23G 3/48* (2013.01); *A23G 4/068* (2013.01); *A24B 13/00* (2013.01); *A24B 15/24* (2013.01); *A24B 15/30* (2013.01); *A24B 15/302* (2013.01); *A61K 9/0056* (2013.01)

(58) Field of Classification Search
CPC ....... A24B 13/00; A24B 15/30; A24B 15/302; A23G 3/004; A23G 1/36; A23G 1/38; A23G 1/48; A23G 4/068; A23G 3/0048; A61K 9/0056
USPC ................................................ 131/356, 352
See application file for complete search history.

(56) References Cited

U.S. PATENT DOCUMENTS

| | | | |
|---|---|---|---|
| 904,521 A | 11/1908 | Ellis | |
| 1,376,586 A | 5/1921 | Schwartz | |
| 3,696,917 A | 10/1972 | Levi | |
| 3,877,468 A | 4/1975 | Lichtneckert et al. | |
| 4,148,325 A | 4/1979 | Solomon et al. | |
| 4,513,756 A | 4/1985 | Pittman et al. | |
| 4,528,993 A | 7/1985 | Sensabaugh et al. | |
| 4,611,608 A * | 9/1986 | Vos .......................... | A24B 3/14 |
| | | | 131/354 |
| 4,624,269 A | 11/1986 | Story et al. | |
| 4,660,577 A | 4/1987 | Sensabaugh et al. | |
| 4,786,502 A | 11/1988 | Chapura et al. | |
| 4,963,359 A | 10/1990 | Haslwanter et al. | |
| 4,987,907 A | 1/1991 | Townend | |
| 4,991,599 A | 2/1991 | Tibbetts | |
| 5,092,352 A | 3/1992 | Sprinkle, III et al. | |
| 5,387,416 A | 2/1995 | White et al. | |
| 5,539,093 A | 7/1996 | Fitzmaurice et al. | |
| 5,668,295 A | 9/1997 | Wahab et al. | |
| 5,705,624 A | 1/1998 | Fitzmaurice et al. | |
| 5,844,119 A | 12/1998 | Weigel | |
| 6,510,855 B1 | 1/2003 | Korte et al. | |
| 6,668,839 B2 | 12/2003 | Williams | |
| 6,730,832 B1 | 5/2004 | Dominguez | |
| 6,834,654 B2 | 12/2004 | Williams | |

(Continued)

FOREIGN PATENT DOCUMENTS

| | | |
|---|---|---|
| CN | 204499484 | 7/2015 |
| CN | 105795522 | 7/2016 |

(Continued)

OTHER PUBLICATIONS

De Roton et al. "Factors Influencing the Formation of Tobacco-Specific Nitrosamines in French Air-Cured Tobaccos in Trials and at the Farm Level," *Beiträage zur Tabakforschung International/Contributions to Tobacco Research*, 2005, vol. 21. No. 6.

Nestor et al. "Role Of Oxides Of Nitrogen In Tobacco-Specific Nitrosamine Formation In Flue-Cured Tobacco," *Beiträge zur Tabalforschung International/Contributions to Tobacco Research*, 2003, vol. 20 No. 7.

Staaf et al. "Formation of Tobacco-Specific Nitrosamines (TSNA) During Air-Curing: Conditions and Control" *Beiträge zur Tabakforschung International/Contributions to Tobacco Research*, 2005, vol. 21, No. 6.

*Primary Examiner* — Galen H Hauth
*Assistant Examiner* — Yana B Krinker
(74) *Attorney, Agent, or Firm* — Womble Bond Dickinson (US) LLP

(57) ABSTRACT

A meltable smokeless tobacco composition configured for insertion into the mouth of a user is provided. The smokeless tobacco composition includes a tobacco material and a lipid having a melting point of about 36° C. to about 45° C. An associated process is also provided. The process includes melting a lipid having a melting point of about 36° C. to about 45° C. to form a molten lipid composition, mixing a tobacco material with the molten lipid composition to form a molten smokeless tobacco composition, and cooling the molten smokeless tobacco composition to form a solidified smokeless tobacco composition.

10 Claims, No Drawings

(56) References Cited

U.S. PATENT DOCUMENTS

| | | |
|---|---|---|
| 6,895,974 B2 | 5/2005 | Peele |
| 6,953,040 B2 | 10/2005 | Atchley et al. |
| 7,014,039 B2 | 3/2006 | Henson et al. |
| 7,025,066 B2 | 4/2006 | Lawson et al. |
| 7,032,601 B2 | 4/2006 | Atchley et al. |
| 7,173,170 B2 | 2/2007 | Liu et al. |
| 7,208,659 B2 | 4/2007 | Colliver et al. |
| 7,230,160 B2 | 6/2007 | Benning et al. |
| D592,956 S | 5/2009 | Thiellier |
| 7,537,110 B2 | 5/2009 | Kutsch et al. |
| D594,154 S | 6/2009 | Patel et al. |
| 7,584,843 B2 | 9/2009 | Kutsch et al. |
| 7,650,892 B1 | 1/2010 | Groves et al. |
| 7,694,686 B2 | 4/2010 | Atchley et al. |
| 2004/0020503 A1 | 2/2004 | Williams |
| 2005/0115580 A1 | 6/2005 | Quinter et al. |
| 2005/0244521 A1 | 11/2005 | Strickland et al. |
| 2006/0037623 A1 | 2/2006 | Lawrence, Jr. |
| 2006/0191548 A1 | 8/2006 | Strickland et al. |
| 2006/0236434 A1 | 10/2006 | Conkling et al. |
| 2007/0062549 A1 | 3/2007 | Holton, Jr. et al. |
| 2007/0186941 A1 | 8/2007 | Holton, Jr. et al. |
| 2007/0186942 A1 | 8/2007 | Strickland et al. |
| 2008/0029110 A1 * | 2/2008 | Dube ............ A24B 13/00 131/274 |
| 2008/0029116 A1 | 2/2008 | Robinson et al. |
| 2008/0029117 A1 | 2/2008 | Mua et al. |
| 2008/0173317 A1 | 7/2008 | Robison et al. |
| 2008/0196730 A1 | 8/2008 | Engstrom et al. |
| 2008/0209586 A1 | 8/2008 | Nielsen |
| 2008/0245377 A1 | 10/2008 | Marshall et al. |
| 2008/0305216 A1 | 12/2008 | Crawford et al. |
| 2008/0308115 A1 | 12/2008 | Zimmermann |
| 2009/0004248 A1 | 1/2009 | Bunick et al. |
| 2009/0014018 A1 | 1/2009 | Sengupta et al. |
| 2009/0014343 A1 | 1/2009 | Clark et al. |
| 2009/0014450 A1 | 1/2009 | Bjorkholm |
| 2009/0025738 A1 | 1/2009 | Mua et al. |
| 2009/0025739 A1 | 1/2009 | Brinkley |
| 2009/0065013 A1 | 3/2009 | Essen et al. |
| 2009/0223989 A1 | 9/2009 | Gelardi |
| 2009/0230003 A1 | 9/2009 | Thiellier |
| 2009/0250360 A1 | 10/2009 | Bellamah et al. |
| 2009/0253754 A1 | 10/2009 | Selmin et al. |
| 2009/0266837 A1 | 10/2009 | Gelardi et al. |
| 2009/0293889 A1 | 12/2009 | Kumar et al. |
| 2010/0084424 A1 | 4/2010 | Gelardi |
| 2010/0124560 A1 | 5/2010 | Hugerth et al. |
| 2010/0133140 A1 | 6/2010 | Bailey |
| 2010/0247586 A1 | 9/2010 | Hugerth et al. |
| 2010/0300463 A1 | 12/2010 | Chen et al. |
| 2011/0139164 A1 | 6/2011 | Mua et al. |
| 2011/0174323 A1 | 7/2011 | Coleman, III et al. |
| 2011/0220130 A1 | 9/2011 | Mua et al. |
| 2011/0318411 A1 | 12/2011 | Luber et al. |
| 2012/0037175 A1 | 2/2012 | Cantrell et al. |
| 2013/0118512 A1 * | 5/2013 | Jackson ............ A24B 15/30 131/370 |
| 2016/0135505 A1 | 5/2016 | Li et al. |
| 2016/0192707 A1 | 7/2016 | Li et al. |
| 2017/0006922 A1 | 1/2017 | Wang et al. |

FOREIGN PATENT DOCUMENTS

| | | | |
|---|---|---|---|
| EP | 2 213 181 | 4/2010 | |
| WO | WO 2004/095959 | 11/2004 | |
| WO | WO 2007/138484 | 12/2007 | |
| WO | WO 2008/103935 A2 | 8/2008 | |
| WO | WO 2009/056609 | 5/2009 | |
| WO | WO 2009/068279 | 6/2009 | |
| WO | WO-2009068279 A1 * | 6/2009 | ............ A23G 3/48 |
| WO | WO 2009/087215 | 7/2009 | |
| WO | WO 2013/090366 | 6/2013 | |
| WO | WO 2013090366 | 6/2013 | |
| WO | WO 2016-161554 | 10/2016 | |

* cited by examiner

US 11,666,083 B2

MELTABLE SMOKELESS TOBACCO COMPOSITION

CROSS-REFERENCE TO RELATED APPLICATIONS

The present application is a continuation of U.S. application Ser. No. 15/988,004, filed May 24, 2018, which is a continuation of U.S. application Ser. No. 14/868,867, filed Sep. 29, 2015, which is a continuation of U.S. application Ser. No. 13/330,929, filed Dec. 20, 2011, which is a continuation-in-part of U.S. application Ser. No. 12/854,342, filed Aug. 11, 2010, which are incorporated by reference herein their entireties.

FIELD OF THE DISCLOSURE

The present disclosure relates to products made or derived from tobacco, or that otherwise incorporate tobacco, and are intended for human consumption. In particular, the disclosure relates to compositions or formulations incorporating tobacco, and that are intended to be employed in a smokeless form.

BACKGROUND OF THE DISCLOSURE

Cigarettes, cigars, and pipes are popular smoking articles that employ tobacco in various forms. Such smoking articles are employed by heating or burning tobacco to generate aerosol (e.g., smoke) that may be inhaled by the smoker. Tobacco may also be enjoyed in a so-called "smokeless" form. Particularly popular smokeless tobacco products are employed by inserting some form of processed tobacco or tobacco-containing formulation into the mouth of the user. See for example, the types of smokeless tobacco formulations, ingredients, and processing methodologies set forth in U.S. Pat. No. 1,376,586 to Schwartz; U.S. Pat. No. 3,696,917 to Levi; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Breslin et al.; US Pat. Pub. Nos. 2004/0020503 to Williams; 2005/0115580 to Quinter et al.; 2005/0244521 to Strickland et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0029117 to Mua et al.; 2008/0173317 to Robinson et al.; 2008/0196730 to Engstrom et al.; 2008/0209586 to Neilsen et al.; 2008/0305216 to Crawford et al.; 2009/0065013 to Essen et al.; and 2009/0293889 to Kumar et al.; PCT WO 04/095959 to Arnarp et al.; and U.S. patent application Ser. No. 12/638,394, filed Dec. 15, 2009, to Mua et al. (now published as US 2011/0139164 to Mua et al.); each of which is incorporated herein by reference. Exemplary smokeless tobacco products include CAMEL Snus, CAMEL Orbs, CAMEL Strips and CAMEL Sticks by R. J. Reynolds Tobacco Company; REVEL Mint Tobacco Packs and SKOAL Snus by U.S. Smokeless Tobacco Company; and MARLBORO Snus and Taboka by Philip Morris USA.

It would be desirable to provide an enjoyable form of a tobacco product, such as a smokeless tobacco product, and to provide processes for preparing tobacco-containing compositions suitable for use in smokeless tobacco products.

SUMMARY OF THE DISCLOSURE

The present disclosure relates to a meltable smokeless tobacco product configured for insertion into the mouth of a user and processes for preparing a smokeless tobacco composition suitable for use in a meltable smokeless tobacco product. The smokeless tobacco composition of the disclosure utilizes a lipid substance to provide a meltable smokeless tobacco product. In one aspect, the smokeless tobacco product is in the form of a solid object including a tobacco material and a lipid substance. The smokeless tobacco composition preferably includes a lipid and a tobacco extract, and may include other ingredients, such as sweeteners, binders, fillers, flavoring agents, disintegration aids, preservatives, and the like. According to one aspect, the tobacco extract is an aqueous tobacco extract in spray-dried or freeze-dried particulate form. The meltable smokeless tobacco composition of the disclosure can be packaged as a plurality of product units in a handheld smokeless tobacco container.

In certain embodiments, it is advantageous to mix a tobacco extract with an extender before drying to improve handling and mixing properties of the dried product. For example, the tobacco extract can be used in the form of a particulate mixture of spray-dried or freeze-dried tobacco extract particles and a second spray-dried or freeze-dried particulate material, such as any of a variety of filler or binder materials (e.g., maltodextrin, cyclodextrin, and natural gums such as gum arabic). The weight ratio of tobacco extract to second particulate material in the final dried product can vary, but typically is about 7:1 to about 1:1, such as about 5:1 to about 2:1.

In one aspect, the disclosure provides a meltable smokeless tobacco composition configured for insertion into the mouth of a user of the product, the tobacco product comprising a tobacco material and a lipid having a melting point of about 36° C. to about 45° C., such as about 38° C. to about 41° C. Suitable lipids for providing melting properties of the meltable smokeless tobacco product include animal or plant derived fat, wax, and oil substances, and the like. An exemplary lipid composition is a plant-derived fat comprising a plurality of saturated or unsaturated fatty acid chains having a carbon length of about 14 to about 20 carbon atoms. In one embodiment, the lipid is a blend of palm kernel oil and palm oil.

The smokeless tobacco composition can further include one or more additional components, such as flavorants, fillers, binders, buffering agents, colorants, humectants, oral care additives, preservatives, syrups, disintegration aids, antioxidants, additives derived from an herbal or botanical source, flow aids, and mixtures thereof. Certain embodiments of the invention include fillers (e.g., isomalt or other sugar alcohols), artificial sweeteners (e.g., sucralose), flavorants (e.g., vanillin, spray-dried menthol), salts (e.g., sodium chloride), and combinations thereof.

Exemplary compositions of the invention include a composition including at least about 2 dry weight percent of tobacco extract; at least about 30 dry weight percent of lipid; at least about 0.1 dry weight percent of at least one sweetener; at least about 30 dry weight percent of at least one filler; and at least about 0.5 dry weight percent of at least one flavorant, based on the total weight of the composition. In another embodiment, the composition include at least about 2 dry weight percent of tobacco extract; at least about 35 dry weight percent of lipid; at least about 0.25 dry weight percent of at least one sweetener; at least about 50 dry weight percent of at least one filler; at least about 0.25 dry weight percent of a salt; and at least about 1.0 dry weight percent of at least one flavorant, based on the total weight of the composition. In a still further embodiment, the invention provides a smokeless tobacco composition including about 2 to about 10 dry weight percent of tobacco extract; about 30 to about 50 dry weight percent of lipid; about 0.1 to about 1 dry weight percent of artificial sweetener; about 30 to about 60 dry weight percent filler; a flavorant in an amount up to about 5 dry weight percent; and sodium chloride in an amount up to about 10 dry weight percent, based on the total dry weight of the smokeless tobacco composition.

In yet another aspect, the disclosure provides a process for preparing a meltable smokeless tobacco composition configured for insertion into the mouth of a user and suitable for use as a smokeless tobacco product. The process includes melting a lipid having a melting point of about 36° C. to about 45° C. to form a molten lipid composition; mixing the tobacco material and optional additional components (e.g., flavorants, binders, fillers, disintegration aids, humectants, and mixtures thereof) with the molten lipid to form a molten smokeless tobacco composition; and cooling the molten smokeless tobacco composition to form a solidified smokeless tobacco composition. The process can include depositing the molten smokeless tobacco composition in a mold so as to form the molten smokeless tobacco composition into a predetermined shape.

As noted previously, the tobacco material can be an aqueous tobacco extract, which can be in spray-dried or freeze-dried particulate form. The spray-dried extract can also comprise a second particulate material. In such embodiments, the process of the invention can further include the step of preparing a spray-dried or freeze-dried mixture of the tobacco extract and the second particulate material by mixing the aqueous tobacco extract with an amount of the second particulate material sufficient to provide a mixture with a solids content of at least about 18 weight percent, and thereafter subjecting the mixture to spray-drying or freeze-drying to form a dry particulate material.

Aspects of the present disclosure thus provide advantages as otherwise detailed herein.

DETAILED DESCRIPTION OF THE PREFERRED EMBODIMENTS

The present disclosure now will be described more fully hereinafter. The disclosure may be embodied in many different forms and should not be construed as limited to the aspects set forth herein; rather, these aspects are provided so that this disclosure will satisfy applicable legal requirements. Like numbers refer to like elements throughout. As used in this specification and the claims, the singular forms "a," "an," and "the" include plural referents unless the context clearly dictates otherwise.

The disclosure provides a smokeless tobacco composition suitable for oral use. The smokeless tobacco composition generally includes a particulate tobacco material and a lipid. Such a composition may be used to provide a meltable smokeless tobacco product for oral use. As used herein, "melt," "melting," and "meltable" refer to the ability of the smokeless tobacco product to change from a solid state to a liquid state. That is, melting occurs when a substance (e.g., the smokeless tobacco product) changes from solid to liquid, usually by the application of heat. The application of heat in regard to the smokeless tobacco product of the present invention is provided by the internal temperature of a user's mouth. Thus, the term "meltable" refers to a product that is capable of liquefying in the mouth of the user as the product changes phase from solid to liquid, and is intended to distinguish products that merely disintegrate in the oral cavity through loss of cohesiveness within the product or products that merely dissolve in the oral cavity as aqueous-soluble components of the product interact with moisture.

In this regard, the melting characteristics of the smokeless tobacco composition embodiments described herein may generally be attributed to a lipid component, such as, for example, a fat, oil, or wax substance (or combination thereof), forming a portion of the smokeless tobacco composition. The lipid components used in the invention can be derived from animal or plant material and typically comprise mostly triglycerides along with lesser amounts of free fatty acids and mono- or di-glycerides. In certain embodiments, the lipid used in the invention is a plant-derived fat material that is solid or semi-solid at room temperature (i.e., at about 25° C.) and which at least partially liquefies when subjected to the temperature of the oral cavity of the user. Such plant-derived fats are comprised primarily of saturated or unsaturated fatty acid chains (most of which are bound within triglyceride structures) having a carbon length of about 10 to about 26 carbon atoms, more typically about 14 to about 20 carbon atoms, and most often about 14 to about 18 carbon atoms. Exemplary fats that can be used include palm oil, palm kernel oil, soybean oil, cottonseed oil, and mixtures thereof. According to some aspects, the lipid substance may be hydrogenated, partially hydrogenated, or non-hydrogenated. In some instances, the lipid substance may include a blend of lipid components. For example, the lipid substance may include a blend of palm oil and palm kernel oil. The lipid substance is typically an individual ingredient separate and distinct from the particulate tobacco material used to form the smokeless tobacco composition.

A variety of methods exist for determining the melting point of lipids. However, many naturally-occurring lipids are not chemically homogenous and, therefore, do not have a true single melting point, i.e., the temperature of transition from the solid to the liquid state. Thus, lipids are sometimes characterized by a melting range. One test for determining the melting point of lipids is the Mettler dropping point method (ASTM Standard D3954, 2010, "Standard Test Method for Dropping Point of Waxes," ASTM International, West Conshohocken Pa., 2003, DOI 10.1520/D3954-94R10, www.astm.org.). Melting temperatures for lipids described herein, or smokeless tobacco products containing such lipids, refer to melting temperature points or ranges determined based on the Mettler dropping point method, unless otherwise specified.

The melting point of the lipid component may be chosen so that the resulting smokeless tobacco product composition has a melting point in an appropriate range to provide the desired melting characteristics when the smokeless tobacco product is placed in the oral cavity of the user. In some embodiments, it may be desirable to use a lipid with a higher melting point so that the final smokeless tobacco product remains substantially solid in the oral cavity during use, meaning the user must chew the product in order to break the product into smaller pieces. In other embodiments, a lower melting point can be selected such that the final product readily melts in the mouth of the user during use. Typically, the melting point of the lipid component will be about 29° C. to about 49° C., often about 36° C. to about 45° C., and most often about 38° C. to about 41° C. In certain embodiments, the melting point of the smokeless tobacco product made using the lipid component will also have a melting point within the above ranges. Use of lipids with a melting point of less than about 36° C. is typically less preferred due to handling concerns. That is, transportation and storage of the smokeless tobacco product made using such a lipid may subject the product to high temperatures that could result in a prematurely melted product. In addition, lipid components (and meltable smokeless tobacco products made therefrom) with a melting point of more than about 41° C. are less preferred in certain embodiments due to less desirable mouthfeel characteristics, such as mouthfeel that can be characterized as waxy.

Lipid substances capable of use pursuant to the present invention are available from, for example, Loders Croklaan and AarhusKarlshamn USA Inc. Exemplary lipid substances include 108-24-B from AarhusKarlshamn USA Inc. (a non-hydrogenated lauric coating fat containing a blend of palm kernel oil and palm oil); PARAMOUNT X from Loders Croklaan (a partially hydrogenated vegetable oil containing a blend of palm kernel oil, soybean oil, and cottonseed oil); CENTERNAL 625 from Loders Croklaan (a vegetable fat); PARAMOUNT C from Loders Croklaan (a lauric coating fat containing partially hydrogenated palm kernel oil with lecithin); KAOKOTE 102 from Loders Croklaan (a lauric coating fat containing partially hydrogenated palm kernel oil); SILKO 35-08 from AarhusKarlshamn USA Inc. (an interesterified hydrogenated lauric fat containing palm kernel oil); CEBES 27-70 from AarhusKarlshamn USA Inc. (a fractionated lauric cocoa butter substitute containing hydrogenated palm kernel oil); CISAO 82-53 from AarhusKarlshamn USA Inc. (a non-hydrogenated palm oil); CEBES 29-21 from AarhusKarlshamn USA Inc. (a fractionated cocoa butter substitute containing palm kernel oil and palm oil); CEBES 27-55 from AarhusKarlshamn USA Inc. (a lauric based fat containing partially hydrogenated palm kernel oil and hydrogenated soybean oil); 108-48-B from AarhusKarlshamn USA Inc. (a non-hydrogenated lauric fat which is a blend of palm kernel oil and palm oil); CEBES 29-07 from AarhusKarlshamn USA Inc. (a fractionated non-hydrogenated cocoa butter substitute); CEBES 21-20 from AarhusKarlshamn USA Inc. (a fractionated lauric cocoa butter substitute); CEBES 29-07 from AarhusKarlshamn USA Inc. (a fractionated lauric cocoa butter substitute); and CISAO 78-33 from AarhusKarlshamn USA Inc. (a non-hydrogenated structuring fat).

The relative amount of lipid substance within the smokeless tobacco composition may vary. Preferably, the amount of lipid substance within the smokeless tobacco composition is at least about 10 percent, at least about 20 percent, or at least about 30 percent, on a dry weight basis of the composition. In certain aspects, the amount of lipid material is less than about 60 percent, less than about 50 percent, or less than about 40 weight percent, on a dry weight basis. Exemplary lipid weight ranges include about 10 to about 60 dry weight percent, more typically about 20 to about 40 dry weight percent.

The products of the disclosure incorporate some form of a plant of the *Nicotiana* species, and most preferably, those compositions or products incorporate some form of tobacco. The selection of the *Nicotiana* species can vary; and in particular, the selection of the types of tobacco or tobaccos may vary. Tobaccos that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Passanda, Cubano, Jatin and Bezuki tobaccos), light air cured (e.g., North Wisconsin and Galpao tobaccos), Indian air cured, Red Russian and *Rustica* tobaccos, as well as various other rare or specialty tobaccos. Descriptions of various types of tobaccos, growing practices and harvesting practices are set forth in *Tobacco Production, Chemistry and Technology*, Davis et al. (Eds.) (1999), which is incorporated herein by reference. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al. and U.S. Pat. No. 7,025,066 to Lawson et al.; US Patent Appl. Pub. Nos. 2006/0037623 to Lawrence, Jr. and 2008/0245377 to Marshall et al.; each of which is incorporated herein by reference. Exemplary *Nicotiana* species include *N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis subsp. Hersperis, N. pauciflora, N. petunioides, N. quadrivalvis, N. repanda, N. rotundifolia, N. solanifolia*, and *N. spegazzinii*.

*Nicotiana* species can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; US Patent Appl. Pub. No. 2006/0236434 to Conkling et al.; and PCT WO 2008/103935 to Nielsen et al.

For the preparation of smokeless and smokable tobacco products, it is typical for harvested plant of the *Nicotiana* species to be subjected to a curing process. Descriptions of various types of curing processes for various types of tobaccos are set forth in *Tobacco Production, Chemistry and Technology*, Davis et al. (Eds.) (1999). Exemplary techniques and conditions for curing flue-cured tobacco are set forth in Nestor et al., *Beitrage Tabakforsch. Int.*, 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.*, 21, 305-320 (2005) and Staaf et al., *Beitrage Tabakforsch. Int.*, 21, 321-330 (2005), which are incorporated herein by reference. Certain types of tobaccos can be subjected to alternative types of curing processes, such as fire curing or sun curing. Preferably, harvested tobaccos that are cured are then aged. As such, tobaccos used for the preparation of tobacco compositions or products most preferably incorporate components of tobaccos that have been cured and aged.

At least a portion of the plant of the *Nicotiana* species (e.g., at least a portion of the tobacco portion) can be employed in an immature form. That is, the plant, or at least one portion of that plant, can be harvested before reaching a stage normally regarded as ripe or mature. As such, for example, tobacco can be harvested when the tobacco plant is at the point of a sprout, is commencing leaf formation, is commencing flowering, or the like.

At least a portion of the plant of the *Nicotiana* species (e.g., at least a portion of the tobacco portion) can be employed in a mature form. That is, the plant, or at least one portion of that plant, can be harvested when that plant (or plant portion) reaches a point that is traditionally viewed as being ripe, over-ripe or mature. As such, for example, through the use of tobacco harvesting techniques conventionally employed by farmers, Oriental tobacco plants can be harvested, burley tobacco plants can be harvested, or Virginia tobacco leaves can be harvested or primed by stalk position.

After harvest, the plant of the *Nicotiana* species, or portion thereof, can be used in a green form (e.g., tobacco can be used without being subjected to any curing process). For example, tobacco in green form can be frozen, subjected to irradiation, yellowed, dried, cooked (e.g., roasted, fried or boiled), or otherwise subjected to storage or treatment for later use. Such tobacco also can be subjected to aging conditions.

The tobacco material may be cased and dried, and then ground to the desired form. For example, in some instances, the tobacco material formulation may be cased with an aqueous casing containing components such as sugars (e.g., fructose, glucose, and sucrose), humectants (e.g., glycerin and propylene glycol), flavoring ingredients (e.g., cocoa and licorice), and the like. Non-aqueous casing components may be applied to the tobacco in amounts of about 1 percent to about 15 percent, based on the dry weight of the tobacco.

The tobacco material is typically used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like. Most preferably, the plant material is relatively dry in form during grinding or milling, using equipment such as hammer mills, cutter heads, air control mills, or the like. For example, tobacco parts or pieces may be ground or milled when the moisture content thereof is less than about 15 weight percent to less than about 5 weight percent. Most preferably, the tobacco material is employed in the form of parts or pieces that have an average particle size less than about 50 microns. In one embodiment, the average particle size of the tobacco particles may be less than or equal to about 25 microns. In some instances, the tobacco particles may be sized to pass through a screen mesh. If desired, air classification equipment may be used to ensure that small sized tobacco particles of the desired sizes, or range of sizes, may be collected. If desired, differently sized pieces of granulated tobacco may be mixed together.

At least a portion of the tobacco material employed in the tobacco composition or product (e.g., the tobacco component) can have the form of an extract. Tobacco extracts can be obtained by extracting tobacco using a solvent having an aqueous character such as distilled water or tap water. As such, aqueous tobacco extracts can be provided by extracting tobacco with water, such that water insoluble pulp material is separated from the aqueous solvent and the water soluble and dispersible tobacco components dissolved and dispersed therein. The tobacco extract can be employed in a variety of forms. For example, the aqueous tobacco extract can be isolated in an essentially solvent free form, such as can be obtained as a result of the use of a spray drying or freeze drying process, or other similar types of processing steps. Alternatively, the aqueous tobacco extract can be employed in a liquid form, and as such, the content of tobacco solubles within the liquid solvent can be controlled by selection of the amount of solvent employed for extraction, concentration of the liquid tobacco extract by removal of solvent, addition of solvent to dilute the liquid tobacco extract, or the like. Exemplary techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. No. 4,351,346 to Brummer et al.; U.S. Pat. No. 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. No. 5,074,319 to White et al.; U.S. Pat. No. 5,099,862 to White et al.; U.S. Pat. No. 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,284,875 to Turpen et al.; U.S. Pat. No. 6,298,859 to Kierulff et al.; U.S. Pat. No. 6,772,767 to Mua et al.; U.S. Pat. No. 6,817,970 to Berit et al.; U.S. Pat. No. 6,906,172 to Bratcher et al.; U.S. Pat. No. 7,034,128 to Turpen et al.; U.S. Pat. No. 7,048,211 to Bratcher et al.; and U.S. Pat. No. 7,337,782 to Thompson; and US Patent Appl. Pub. Nos. 2008/0029110 to Dube et al.; 2008/0173317 to Robinson et al.; 2009/0025738 to Mua et al.; 2011/0139164 to Mua et al.; 2011/0247640 to Beeson et al., all of which are incorporated by reference herein.

In some embodiments utilizing a tobacco extract in spray-dried or freeze-dried particulate form, it is useful to mix the tobacco extract with an extender component (e.g., any of the filler or binder components noted herein such as maltodextrin, cyclodextrin, or a natural gum such as gum arabic) prior to the drying process to form a particulate dried mixture that can exhibit improved mixing properties, resulting in a more homogeneous final product. Spray-dried tobacco extracts tend to have a low density and poor flowability, which makes handling of the extract more challenging in a manufacturing process. Accordingly, in certain embodiments, an extender component can be added to the aqueous tobacco extract in an amount sufficient to raise the pre-drying solids content of the aqueous composition to about 18 to about 22 percent by weight (e.g., at least about 18 or at least about 20 percent by weight). Thereafter, the combined mixture can be spray-dried or freeze-dried, and the resulting material will typically have a weight ratio of extract to extender of about 7:1 to about 1:1, more often about 5:1 to about 2:1 (e.g., about 3:1).

The relative amount of tobacco material (e.g., a milled tobacco material or an aqueous tobacco extract) within the smokeless tobacco composition may vary, but tobacco material is typically the predominate ingredient. Preferably, the amount of tobacco material formulation within the smokeless tobacco composition is at least about 25 percent or at least about 30 percent, on a dry weight basis of the composition. In certain instances, the amounts of other components within the smokeless tobacco composition may exceed about 40 percent, on a dry weight basis. A typical range of tobacco material formulation within the smokeless tobacco composition is about 25 to about 60 dry weight percent, more typically about 30 to about 40 dry weight percent.

However, smaller amounts of tobacco material can be employed, particularly where the tobacco is used in the form of a concentrated tobacco extract. For example, some embodiments of the present invention comprises at least about 1 dry weight percent, at least about 2 dry weight percent, or at least about 3 dry weight percent of tobacco extract (e.g., about 1 to about 10 dry weight percent of tobacco extract).

The moisture content of the tobacco material formulation prior to mixing with the lipid substance to form the smokeless tobacco composition may vary. Most preferably, the moisture content of the tobacco material formulation is less than about 10 weight percent, and may be less than about 6 percent, and is often less than about 3 weight percent. The manner by which the moisture content of the tobacco material formulation is controlled may vary. For example the tobacco material formulation may be subjected to thermal or convection heating. As a specific example, the tobacco material formulation may be oven-dried, in warmed air at temperatures of about 40° C. to about 95° C. for a length of time appropriate to attain the desired moisture content. For example, the tobacco material formulation may be dried for about 12 hours to about 24 hours at about 54° C. to about 60° C.

In some instances, prior to preparation of the tobacco material formulation, the tobacco parts or pieces may be irradiated, or those parts and pieces may be pasteurized, or otherwise subjected to controlled heat treatment. Additionally, if desired, after preparation of all or a portion of the tobacco material formulation, the component materials may be irradiated, or those component materials may be pasteurized, or otherwise subjected to controlled heat treatment. For example, a tobacco material formulation may be prepared, followed by irradiation or pasteurization, and then flavoring ingredient(s) may be applied to the formulation. Representative processes are set forth in US Pat. Pub. Nos. 2009/0025738 to Mua et al.; 2009/0025739 to Brinkley et al.; and 2011/0247640 to Beeson et al., which are incorporated herein by reference.

In one embodiment, a moist tobacco material is subjected to a heat treatment (e.g., heating the moist tobacco material at a temperature of at least about 100° C.) after mixing the tobacco material with one or more additives selected from the group consisting of lysine, glycine, histidine, alanine, methionine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality (e.g., cysteine), oxidizing agents, oxidation catalysts, natural plant extracts (e.g., rosemary extract), and combinations thereof. Such a heat treatment process is described in US Pat. Pub. No. 2010/0300463 to Chen et al., which is incorporated by reference herein.

In certain embodiments, the tobacco extract used in the invention is a heat-treated tobacco extract that has been treated prior to inclusion in the smokeless tobacco product by heating the tobacco extract in an aqueous solution comprising lysine, cysteine, asparaginase, or hydrogen peroxide. The aqueous solution can comprise additional additives; for example, in some embodiments, the aqueous solution further comprises NaOH. In one exemplary embodiment, a smokeless tobacco product is provided, wherein the tobacco extract is a heat-treated tobacco extract that has been treated prior to inclusion in the smokeless tobacco product by heating the tobacco extract in an aqueous solution comprising L-lysine and NaOH.

The tobacco material formulation used for the manufacture of the smokeless tobacco product also can be processed, blended, formulated, combined and mixed with other materials or ingredients. See, for example, those representative components, combination of components, relative amounts of those components and ingredients relative to tobacco, and manners and methods for employing those components, set forth in US Pat. Pub. Nos. 2007/0062549 to Holton, et al. and 2007/0186941 to Holton, et al. and, each of which is incorporated herein by reference.

The additives can be artificial, or can be obtained or derived from herbal or biological sources. Exemplary types of additives include salts (e.g., sodium chloride, potassium chloride, sodium citrate, potassium citrate, sodium acetate, potassium acetate, and the like), natural sweeteners (e.g., fructose, sucrose, glucose, maltose, vanillin, ethylvanillin glucoside, mannose, galactose, lactose, and the like), artificial sweeteners (e.g., sucralose, saccharin, aspartame, acesulfame K, neotame and the like), organic and inorganic fillers (e.g., grains, processed grains, puffed grains, maltodextrin, cyclodextrin, dextrose, calcium carbonate, calcium phosphate, corn starch, lactose, sugar alcohols such as isomalt, mannitol, erythritol, xylitol, or sorbitol, finely divided cellulose, and the like), binders (e.g., povidone, sodium carboxymethylcellulose and other modified cellulosic types of binders, sodium alginate, xanthan gum, starch-based binders, gum arabic, lecithin, and the like), pH adjusters or buffering agents (e.g., metal hydroxides, preferably alkali metal hydroxides such as sodium hydroxide and potassium hydroxide, and other alkali metal buffers such as metal carbonates, preferably potassium carbonate or sodium carbonate, or metal bicarbonates such as sodium bicarbonate, and the like), colorants (e.g., dyes and pigments, including caramel coloring, titanium dioxide, and the like), humectants (e.g., glycerin, propylene glycol, and the like), oral care additives (e.g., thyme oil, eucalyptus oil, and zinc), preservatives (e.g., potassium sorbate and the like), syrups (e.g., honey, high fructose corn syrup, and the like), disintegration or compressibility aids (e.g., microcrystalline cellulose, croscarmellose sodium, crospovidone, sodium starch glycolate, pregelatinized corn starch, and the like), flavorant and flavoring mixtures, antioxidants, and mixtures thereof.

Such additives may be preferably provided in a powder or granulated form for mixing with the tobacco material, prior to mixing with the lipid substance. Most preferably, the additive is employed in the form of parts or pieces that have an average particle size less than about 50 microns. According to some aspects, the average particle size of the additive may be about 25 microns or less. The moisture content of additives may vary. Most preferably, the moisture content of the additive is less than about 10 weight percent, and may be less than about 6 percent, and is often less than about 3 weight percent. The additive may be admixed with the particulate tobacco material in, for example, a Hobart mixer with a paddle prior to mixing with the lipid substance. The relative amounts of the various additive components within the smokeless tobacco composition may vary.

The aforementioned types of additives can be employed together (e.g., as additive formulations) or separately (e.g., individual additive components can be added at different stages involved in the preparation of the final tobacco product). The relative amounts of the various components within the smokeless tobacco formulation may vary, and typically are selected so as to provide the desired sensory and performance characteristics to the tobacco product.

As used herein, a "flavorant" or "flavoring agent" is any flavorful or aromatic substance capable of altering the sensory characteristics associated with the smokeless tobacco composition. Exemplary sensory characteristics that can be modified by the flavorant include, taste, mouthfeel, moistness, coolness/heat, and/or fragrance/aroma. The flavorants can be natural or synthetic, and the character of these flavors can be described as, without limitation, fresh, sweet, herbal, confectionary, floral, fruity or spice. Specific types of flavors include, but are not limited to, vanilla, coffee, chocolate, cream, mint, spearmint, menthol, peppermint, wintergreen, lavender, cardamon, nutmeg, cinnamon, clove, cascarilla, sandalwood, honey, jasmine, ginger, anise, sage, licorice, lemon, orange, apple, peach, lime, cherry, and strawberry. Flavorants utilized in the invention also can include components that are considered moistening, cooling or smoothening agents, such as eucalyptus. These flavors may be provided neat (i.e., alone) or in a composite (e.g., spearmint and menthol or orange and cinnamon). In some instances, the flavorant may be provided in a spray-dried form. In other instances, the flavorant may be provided in liquid form. Flavorants are typically present in an amount of about 0.5 to about 10 dry weight percent, often about 1 to about 6 dry weight percent, and most often about 2 to about 5 dry weight percent.

Sweeteners can be used in natural or artificial form or as a combination of artificial and natural sweeteners. In one embodiment, sucralose is a primary sweetener ingredient. When present, a representative amount of sweetener, whether an artificial sweetener and/or natural sugar, may make up at least about 1 percent to at least about 5 percent, of the total dry weight of the composition. Preferably, the amount of sweetener within the composition will not exceed about 40 percent, often will not exceed about 35 percent, and frequently will not exceed about 30 percent, of the total dry weight of the composition.

A non-sweetener flavorant preferably may be employed in amounts sufficient to provide desired sensory attributes to the smokeless tobacco composition. When present, a representative amount of flavorant (e.g., vanillin) may make up less than about 1 percent of the total dry weight of the composition.

The smokeless tobacco compositions of the invention will typically include at least one filler ingredient. Such components of the composition often fulfill multiple functions, such as enhancing certain organoleptic properties such as texture and mouthfeel, enhancing cohesiveness or compressibility of the product, and the like. Certain aspects of the disclosure utilize sugar alcohol components such as isomalt. When present, a representative amount of filler, whether an organic and/or inorganic filler, may make up at least about 20 percent to at least about 40 percent, of the total dry weight of the composition. Preferably, the amount of filler within the composition will not exceed about 60 percent, and frequently will not exceed about 40 percent, of the total dry weight of the composition. In one embodiment, a sugar alcohol such as isomalt is provided as a filler.

A salt (e.g., sodium chloride) may be employed in amounts sufficient to provide desired sensory attributes to the smokeless tobacco composition. When present, a representative amount of salt will typically be used in an amount up to about 10 percent of the total dry weight of the composition, more typically up to about 5 percent or up to about 2 percent.

Any of the above-noted classes of ingredients for the smokeless tobacco composition of the disclosure can be derived from tobacco material by subjecting at least a portion of a tobacco plant (e.g., leaves, seeds, flowers, stalks, roots, or stems) to a separation process, which typically can include multiple sequential extraction steps, in order to isolate desired components of the tobacco material. Exemplary separation processes include chromatography, distillation, filtration, recrystallization, solvent-solvent partitioning, cold pressing, solvent extraction (e.g., using solvents such as water, alcohols or hydrocarbons such as heptane or hexane), or a combination thereof. The resulting isolated tobacco component can be chemically transformed prior to use in the compositions of the disclosure. Exemplary chemical transformations include hydrogenation, esterification, transesterification, isomeric conversion, acetal formation, acetal decomposition, acid/base reaction, hydrolysis, thermal treatment, enzymatic treatment, and combinations of such steps. Techniques for preparing tobacco isolates for use in the compositions of the disclosure are set forth, for example, in U.S. Pat. Pub. Nos. 2011/0174323 to Coleman, III et al., and 2011/0259353 to Coleman, III et al., which are incorporated by reference herein in their entirety. Examples of the types of compounds that may be present in the tobacco isolate include hydrocarbons, cellulose, alcohols, aldehydes, ketones, carboxylic acids, amino acids, esters, lactones, anhydrides, carbohydrates (e.g., reducing sugars), phenols, quinones, ethers, nitriles, amines, amides, imides, plastid pigments, proteins, coenzyme-Q, pectin, starch, lignin, and lipids. Additional examples are described as natural tar diluents in PCT WO 2007/012980 to Lipowicz, which is incorporated by reference herein in its entirety. The type or function of a smokeless tobacco ingredient prepared from a tobacco isolate will vary depending on the composition of the isolate, which can vary in part based on the extraction process employed, the portion of the tobacco plant involved, the type of chemical transformation utilized, and the like. Certain tobacco isolates can provide sugars, fillers, binders, disintegration or compressibility aids, or flavorants for the smokeless tobacco composition of the disclosure.

Representative smokeless tobacco compositions may incorporate about 25 to about 45 percent tobacco, about 10 to about 50 percent lipid component, about 0 to about 1 percent artificial sweetener, about 20 to about 40 percent filler, a flavorant in an amount of up to about 10 percent, and salt in an amount up to about 10 percent, based on the total dry weight of the smokeless tobacco composition. The particular percentages and choice of ingredients will vary depending upon the desired flavor, texture, and other characteristics.

The manner by which the various components of the smokeless tobacco composition are combined may vary. The various components of the smokeless tobacco composition may be contacted, combined, or mixed together in conical-type blenders, mixing drums, ribbon blenders, or the like, such as a Hobart mixer. As such, the overall mixture of various components with the powdered tobacco components may be relatively uniform in nature. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference.

The manner by which the various components of the meltable smokeless tobacco composition are combined may vary. In one embodiment, the particulate tobacco material and any additives admixed therewith are provided in a dry form. That is, the particulate tobacco material and any additives preferably have a moisture content of less than about 10 percent, and preferably less than about 6 percent. All dry ingredients, in powder form, as well the dried particulate tobacco material, are added together and thoroughly mixed.

The lipid is typically melted in a mixing vessel to form a molten lipid composition. While maintaining heat to the mixing vessel having the molten lipid composition, the mixed dry formulation is added while vigorous mixing occurs, thereby forming a molten smokeless tobacco composition slurry having a moisture content of less than about 10 percent, and preferably less than about 5 percent. The slurry may be deposited in a mold (plastic, metal, etc.) to achieve a desired product size such as about 0.5 to about 1 gram weight per piece of smokeless tobacco product. In some instances, a Racine Depositor and a piston type jacketed depositor may be used for this type of application. The slurry may be deposited at varying temperatures, depending on the lipid substance used. Typically, in non-tempered lipid substances, the depositing temperature may be about 0.5 to about 1 degree Celsius above the melting point of the lipid substance. In some preferred embodiments, the depositing temperature of the slurry may be about 38° C. to about 41° C. According to some aspects, the mold trays may be placed into a cooling tunnel at about 10° C. to about 15° C. for approximately 5-10 minutes. The slurry may then be allowed to harden by ambient air drying, after which the individual pieces of smokeless tobacco product may be removed from the mold. According to some aspects, the rate of hardening of the smokeless tobacco composition can be increased by using refrigerated temperatures, such as, for example, about 4° C. to cool the slurry.

According to some embodiments, the smokeless tobacco composition may be coated with a coating substance. For example, a glazing or anti-sticking coating substance, such as, for example, CAPOL 410 (available from Centerchem, Inc.), may be applied to the smokeless tobacco composition to provide free-flowing properties. Outer coatings can also help to improve storage stability of the smokeless tobacco products of the present disclosure as well as improve the packaging process by reducing friability and dusting. Devices for providing outer coating layers to the products of the present disclosure include pan coaters and spray coaters, and particularly include the coating devices available as CompuLab 24, CompuLab 36, Accela-Cota 48 and Accela-Cota 60 from Thomas Engineering.

An exemplary outer coating comprises a film-forming polymer, such as a cellulosic polymer, an optional plasticizer, and optional flavorants, colorants, salts, sweeteners or other additives of the types set forth herein. The coating compositions are usually aqueous in nature and can be applied using any pellet or tablet coating technique known in the art, such as pan coating. Exemplary film-forming polymers include cellulosic polymers such as methylcellulose, hydroxypropyl cellulose (HPC), hydroxypropyl methylcellulose (HPMC), hydroxyethyl cellulose, and carboxy methylcellulose. Exemplary plasticizers include aqueous solutions or emulsions of glyceryl monostearate and triethyl citrate. Exemplary coating compositions and methods of application are described in U.S. application Ser. No. 12/876,785 to Hunt et al.; filed Sep. 7, 2010, and which is incorporated by reference herein.

Although the foregoing description focuses on compositions that are uniform throughout each product unit, products can also be formed with multiple different formulations having different properties in the same product unit. For example, two different compositions could be co-extruded to form a product with different characteristics across its cross-section. Such a process could be used to provide a product with two different compositions featuring different melting rates such that a first portion of the product melts at a first rate (e.g., a faster rate) and a second portion melts at a second, slower rate.

According to some aspects, the tobacco component of the smokeless tobacco composition can be replaced or supplemented with other suitable botanical components such as, for example, tea particulates, coffee particulates, herbal particulates, spice particulates and/or combinations thereof. The particulates may be typically provided in a powder form, which may be extracted from an appropriate botanical source.

The smokeless tobacco composition can be provided in any suitable predetermined shape or form, and most preferably is provided as a molded product (e.g., formed in the general shape of a pill, pellet, tablet, sheet, coin, bead, ovoid, obloid, cylinder, bean, stick, rod, cube, or the like). The mouthfeel of certain embodiments of the smokeless tobacco product can be characterized by a smooth and creamy texture. According to one aspect, the smokeless tobacco product is capable of lasting in the user's mouth without chewing for about 2-3 minutes, meaning the user of the product is formulated for enjoyment in the oral cavity of about 2 to about 3 minutes before swallowing.

Certain smokeless tobacco compositions can incorporate tobacco as the major component thereof. In certain embodiments, those compositions do not, to any substantial degree, leave any residue in the mouth of the user thereof. In addition, certain embodiments of those compositions do not provide the user's mouth with a slick, waxy or slimy sensation, but instead provide a smooth and creamy sensation when in the mouth of the user.

Products of the present invention may be packaged and stored in any suitable packaging. See, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 7,946,450 to Gelardi et al.; U.S. Pat. No. 8,033,425 to Gelardi; U.S. Pat. No. 8,066,123 to Gelardi; D592,956 to Thiellier; D594,154 to Patel et al.; and D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0230003 to Thiellier; 2010/0084424 to Gelardi; 2010/0133140 to Bailey et al; 2010/0264157 to Bailey et al.; 2011/0168712 to Gelardi et al.; and 2011/0204074 to Bailey et al., which are incorporated herein by reference.

The following examples are provided to illustrate further aspects associated with the present disclosure, but should not be construed as limiting the scope thereof. Unless otherwise noted, all parts and percentages are by dry weight.

EXPERIMENTAL

Example 1

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), a salt (sodium chloride), a sweetener (sucralose), and flavorants (vanillin, spray-dried peppermint, spray-dried menthol). All dry ingredients, in powder form, as well the dried tobacco material, are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing a blend of palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34 parts lipid substance, 25.5 parts filler, 36 parts tobacco material, 0.5 parts salt, 0.45 parts sweetener, and 3.55 parts flavorant.

Example 2

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), a salt (sodium chloride), a sweetener (sucralose), and flavorants (vanillin, spray-dried peppermint, spray-dried menthol). All dry ingredients, in powder form, as well the dried tobacco material, are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing a blend of palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34 parts lipid substance, 24.5 parts filler, 36 parts tobacco material, 0.5 parts salt, 0.45 parts sweetener, and 4.55 parts flavorant.

Example 3

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), a salt (sodium chloride), a sweetener (sucralose), and flavorants (vanillin, spray-dried peppermint, spray-dried menthol). All dry ingredients, in powder form, as well the dried tobacco material, are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing a blend of palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34 parts lipid substance, 23.5 parts filler, 36 parts tobacco material, 0.5 parts salt, 0.45 parts sweetener, and 5.55 parts flavorant.

Example 4

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), a sweetener (sucrose powder), and a flavorant (mint oil). All dry ingredients, in powder form, as well the dried tobacco material, are added together and thoroughly mixed in a Hobart mixer with a paddle for about three minutes at about 120 rpm.

A lipid substance having a melting point of about 43° C. to about 47° C. is provided (available as PARAMOUNT X from Loders Croklaan). The lipid substance is a partially hydrogenated vegetable oil containing a blend of palm kernel oil, soybean oil, and cottonseed oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 40 parts lipid substance, 29.15 parts filler, 30 parts tobacco material, 0.5 parts sweetener, and 0.35 parts flavorant.

Example 5

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), a sweetener (sucrose powder), and a flavorant (mint oil). All dry ingredients, in powder form, as well the dried tobacco material, are added together and thoroughly mixed in a Hobart mixer with a paddle for about three minutes at about 120 rpm.

A lipid substance having a melting point of about 31° C. to about 33° C. is provided (available as CENTERNAL 625 from Loders Croklaan). The lipid substance is a vegetable fat. The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 40 parts lipid substance, 29.15 parts filler, 30 parts tobacco material, 0.5 parts sweetener, and 0.35 parts flavorant.

Example 6

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), additives (sodium chloride, flour), a sweetener (sucralose), an emulsifier (Polyglycerol Polyricinoleate (PGPR)), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 37° C. to about 40° C. is provided (available as PARAMOUNT C from Loders Croklaan). The lipid substance is a lauric coating fat containing partially hydrogenated palm kernel oil with lecithin.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 32.6 parts lipid substance (0.4 parts lecithin), 33.2 parts filler, 31.9 parts tobacco material, 1.72 parts additive, 0.43 parts sweetener, 0.08 parts emulsifier, and 0.04 parts flavorant.

Example 7

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), additives (sodium chloride, flour), a sweetener (sucralose), an emulsifier (Polyglycerol Polyricinoleate (PGPR)), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 37° C. to about 40° C. is provided (available as PARAMOUNT C from Loders Croklaan). The lipid substance is a lauric coating fat containing partially hydrogenated palm kernel oil with lecithin.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 41.5 parts lipid substance (0.4 parts lecithin), 24.5 parts filler, 31.5 parts tobacco material, 1.8 parts additive, 0.45 parts sweetener, 0.08 parts emulsifier, and 0.05 parts flavorant.

Example 8

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), additives (sodium chloride, flour), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 37° C. to about 40° C. is provided (available as PARAMOUNT C from Loders Croklaan). The lipid substance is a lauric coating fat containing partially hydrogenated palm kernel oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 33.78 parts lipid substance, 24.48 parts filler, 40 parts tobacco material, 1.25 parts additive, 0.45 parts sweetener, and 0.04 parts flavorant.

Example 9

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), additives (sodium chloride, flour), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 37° C. to about 40° C. is provided (available as PARAMOUNT C from Loders Croklaan). The lipid substance is a lauric coating fat containing partially hydrogenated palm kernel oil with lecithin.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 36.58 parts lipid substance (0.45 parts lecithin), 24.56 parts filler, 36.56 parts tobacco material, 1.81 parts additive, 0.45 parts sweetener, and 0.04 parts flavorant.

Example 10

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 39° C. to about 40° C. is provided (available as KAOKOTE 102 from Loders Croklaan). The lipid substance is a non-lauric fat containing partially hydrogenated soybean or cottonseed oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 24.79 parts filler, 40.51 parts tobacco material, 0.45 parts sweetener, and 0.04 parts flavorant.

Example 11

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 39° C. to about 40° C. is provided (available as KAOKOTE 102 from Loders Croklaan). The lipid substance is a non-lauric fat containing partially hydrogenated soybean or cottonseed oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 24.49 parts filler, 40.51 parts tobacco material, 0.75 parts sweetener, and 0.04 parts flavorant.

Example 12

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 39° C. to about 40° C. is provided (available as KAOKOTE 102 from Loders Croklaan). The lipid substance is a non-lauric fat containing partially hydrogenated soybean or cottonseed oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 24.24 parts filler, 40.51 parts tobacco material, 1 part sweetener, and 0.04 parts flavorant.

Example 13

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 3.4 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 38° C. to about 40° C. is provided (available as SILKO 35-08 from AarhusKarlshamn USA Inc.). The lipid substance is a lauric cocoa butter substitute containing hydrogenated palm kernel oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 24.79 parts filler, 40.51 parts tobacco material, 0.45 parts sweetener, and 0.04 parts flavorant.

Example 14

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 36° C. to about 40° C. is provided (available as CEBES 27-70 from AarhusKarlshamn USA Inc.). The lipid substance is a fractionated lauric cocoa butter substitute containing hydrogenated palm kernel oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 24.79 parts filler, 40.51 parts tobacco material, 0.45 parts sweetener, and 0.04 parts flavorant.

Example 15

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance blend is provided. A first lipid substance having a melting point of about 36° C. to about 40° C. is provided (available as CEBES 27-70 from AarhusKarlshamn USA Inc.). The first lipid substance is a fractionated lauric cocoa butter substitute containing hydrogenated palm kernel oil. A second lipid substance having a melting point of about 53° C. to about 57° C. is provided (available as CISAO 82-53 from AarhusKarlshamn USA Inc.). The second lipid substance is a non-hydrogenated palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 32.71 parts first lipid substance, 1.5 parts second lipid substance, 29.79 parts filler, 35.51 parts tobacco material, 0.45 parts sweetener, and 0.04 parts flavorant.

Example 16

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance blend is provided. A first lipid substance having a melting point of about 36° C. to about 40° C. is provided (available as CEBES 27-70 from AarhusKarlshamn USA Inc.). The first lipid substance is a fractionated lauric cocoa butter substitute containing hydrogenated palm kernel oil. A second lipid substance having a melting point of about 53° C. to about 57° C. is provided (available as CISAO 82-53 from AarhusKarlshamn USA Inc.). The second lipid substance is a non-hydrogenated palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 31.21 parts first lipid substance, 3 parts second lipid substance, 29.79 parts filler, 35.51 parts tobacco material, 0.45 parts sweetener, and 0.04 parts flavorant.

Example 17

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance blend is provided. A first lipid substance having a melting point of about 36° C. to about 40° C. is provided (available as CEBES 27-70 from AarhusKarlshamn USA Inc.). The first lipid substance is a fractionated lauric cocoa butter substitute containing hydrogenated palm kernel oil. A second lipid substance having a melting point of about 53° C. to about 57° C. is provided (available as CISAO 82-53 from AarhusKarlshamn USA Inc.). The second lipid substance is a non-hydrogenated palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 30.21 parts first lipid substance, 4 parts second lipid substance, 29.79 parts filler, 35.51 parts tobacco material, 0.45 parts sweetener, and 0.04 parts flavorant.

Example 18

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance blend is provided. A first lipid substance having a melting point of about 36° C. to about 40° C. is provided (available as CEBES 27-70 from AarhusKarlshamn USA Inc.). The first lipid substance is a fractionated lauric cocoa butter substitute containing hydrogenated palm kernel oil. A second lipid substance having a melting point of about 53° C. to about 57° C. is provided (available as CISAO 82-53 from AarhusKarlshamn USA Inc.). The second lipid substance is a non-hydrogenated palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 29.21 parts first lipid substance, 5 parts second lipid substance, 29.79 parts filler, 35.51 parts tobacco material, 0.45 parts sweetener, and 0.04 parts flavorant.

Example 19

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance blend is provided. A first lipid substance having a melting point of about 36° C. to about 40° C. is provided (available as CEBES 27-70 from AarhusKarlshamn USA Inc.). The first lipid substance is a fractionated lauric cocoa butter substitute containing hydrogenated palm kernel oil. A second lipid substance having a melting point of about 53° C. to about 57° C. is provided (available as CISAO 82-53 from AarhusKarlshamn USA Inc.). The second lipid substance is a non-hydrogenated palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 24.21 parts first lipid substance, 10 parts second lipid substance, 29.79 parts filler, 35.51 parts tobacco material, 0.45 parts sweetener, and 0.04 parts flavorant.

Example 20

A smokeless tobacco composition suitable for use as a meltable smokeless tobacco product for oral use is provided in the following manner.

A tobacco material having tobacco particles with an average particle size of about 30 microns is provided. The tobacco material is dried at about 60° C. to reduce the moisture content from about 50 percent to about 6.5 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance blend is provided. A first lipid substance having a melting point of about 36° C. to about 40° C. is provided (available as CEBES 27-70 from AarhusKarlshamn USA Inc.). The first lipid substance is a fractionated lauric cocoa butter substitute containing hydrogenated palm kernel oil. A second lipid substance having a melting point of about 53° C. to about 57° C. is provided (available as CISAO 82-53 from AarhusKarlshamn USA Inc.). The second lipid substance is a non-hydrogenated palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 14.21 parts first lipid substance, 20 parts second lipid substance, 29.79 parts filler, 35.51 parts tobacco material, 0.45 parts sweetener, and 0.04 parts flavorant.

Example 21

A smokeless tobacco composition suitable for use as a meltable smokeless tobacco product for oral use is provided in the following manner.

A tobacco material having tobacco particles with an average particle size of about 30 microns is provided. The tobacco material is dried at about 54° C. for about 24 hours to reduce the moisture content from about 50 percent to less than about 3 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 40° C. to about 44° C. is provided (available as CEBES 29-21 from AarhusKarlshamn USA Inc.). The lipid substance is a fractionated cocoa butter substitute containing palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 24.79 parts filler, 40.51 parts tobacco material, 0.45 parts sweetener, and 0.04 parts flavorant.

Example 22

A smokeless tobacco composition suitable for use as a meltable smokeless tobacco product for oral use is provided in the following manner.

A tobacco material having tobacco particles with an average particle size of about 30 microns is provided. The tobacco material is dried at about 54° C. for about 24 hours to reduce the moisture content from about 50 percent to less than about 3 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 34° C. to about 37° C. is provided (available as CEBES 27-55 from AarhusKarlshamn USA Inc.). The lipid substance is a partially hydrogenated palm kernel oil and soybean oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 24.79 parts filler, 40.51 parts tobacco material, 0.45 parts sweetener, and 0.04 parts flavorant.

Example 23

A smokeless tobacco composition suitable for use as a meltable smokeless tobacco product for oral use is provided in the following manner.

A tobacco material having tobacco particles with an average particle size of about 30 microns is provided. The tobacco material is dried at about 54° C. for about 24 hours to reduce the moisture content from about 50 percent to less than about 3 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 40° C. to about 44° C. is provided (available as CEBES 29-21 from AarhusKarlshamn USA Inc.). The lipid substance is a fractionated cocoa butter substitute containing palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 29.79 parts filler, 35.51 parts tobacco material, 0.45 parts sweetener, and 0.04 parts flavorant.

Example 24

A smokeless tobacco composition suitable for use as a meltable smokeless tobacco product for oral use is provided in the following manner.

A tobacco material having tobacco particles with an average particle size of about 30 microns is provided. The tobacco material is dried at about 54° C. for about 24 hours to reduce the moisture content from about 50 percent to less than about 3 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 34° C. to about 37° C. is provided (available as CEBES 27-55 from AarhusKarlshamn USA Inc.). The lipid substance is a partially hydrogenated palm kernel oil and soybean oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 29.79 parts filler, 35.51 parts tobacco material, 0.45 parts sweetener, and 0.04 parts flavorant.

Example 25

A smokeless tobacco composition suitable for use as a meltable smokeless tobacco product for oral use is provided in the following manner.

A tobacco material having tobacco particles with an average particle size of about 30 microns is provided. The tobacco material is dried at about 54° C. for about 24 hours to reduce the moisture content from about 50 percent to less than about 3 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 40° C. to about 44° C. is provided (available as CEBES 29-21 from AarhusKarlshamn USA Inc.). The lipid substance is a fractionated cocoa butter substitute containing palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 36.68 parts lipid substance, 23.86 parts filler, 38.99 parts tobacco material, 0.43 parts sweetener, and 0.04 parts flavorant.

Example 26

A smokeless tobacco composition suitable for use as a meltable smokeless tobacco product for oral use is provided in the following manner.

A tobacco material having tobacco particles with an average particle size of about 30 microns is provided. The tobacco material is dried at about 54° C. for about 24 hours to reduce the moisture content from about 50 percent to less than about 3 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 24.79 parts filler, 40.51 parts tobacco material, 0.45 parts sweetener, and 0.04 parts flavorant.

Example 27

A smokeless tobacco composition suitable for use as a meltable smokeless tobacco product for oral use is provided in the following manner.

A tobacco material having tobacco particles with an average particle size of about 30 microns is provided. The tobacco material is dried at about 54° C. for about 24 hours to reduce the moisture content from about 50 percent to less than about 3 percent. Various dry ingredients are provided, which include a filler (isomalt), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34.21 parts lipid substance, 29.79 parts filler, 35.51 parts tobacco material, 0.45 parts sweetener, and 0.04 parts flavorant.

Example 28

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), additives (sodium chloride, flour), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34 parts lipid substance, 29 parts filler, 36 parts tobacco material, 0.5 parts additive, 0.45 parts sweetener, and 0.05 parts flavorant.

Example 29

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (isomalt), additives (sodium chloride, flour), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 39° C. to about 41° C. is provided (available as 108-48-B from AarhusKarlshamn USA Inc.). The lipid substance is non-hydrogenated lauric coating fat containing palm kernel oil and palm oil.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 34 parts lipid substance, 29 parts filler, 36 parts tobacco material, 0.5 parts additive, 0.45 parts sweetener, and 0.05 parts flavorant.

Example 30

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a sweetener (sucrose), a salt (sodium chloride), a filler (erythritol), a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 27° C. to about 34° C. is provided (available as cocoa butter from Barry Callebaut CB302). The lipid substance is de-odorized natural cocoa butter.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 45 parts lipid substance, 9 parts filler, 30 parts tobacco material, 2 parts salt, 14 parts sweetener, and 0.01 parts flavorant.

Example 31

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a sweetener/filler (xylitol, erythritol, isomalt), a salt (sodium chloride), a sweetener (sucralose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 27° C. to about 34° C. is provided (available as cocoa butter from Barry Callebaut CB302). The lipid substance is de-odorized natural cocoa butter.

The lipid substance is melted in a mixing vessel. While maintaining heat to the mixing vessel having the melted lipid substance, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 45 parts lipid substance, 22.83 parts filler, 30 parts tobacco material, 2 parts salt, 0.16 parts sweetener, and 0.01 parts flavorant.

Example 32

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (erythritol), a salt (sodium chloride), a sweetener (sucrose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 27° C. to about 34° C. is provided (available from Barry Callebaut CB302) and a second lipid having a melting point of about 33° C. to 37° C. (available as CEBES 21-25 from AarhusKarlshamn USA Inc.). The lipid substance CB302 is de-odorized natural cocoa butter and CEBES 21-25 is mix of palm kernel oil and hydrogenated palm oil.

The lipid substance is melted in a mixing vessel. While maintaining heat to the mixing vessel having the melted lipid substance, a small amount of glycerin is added as a processing aid. Following the glycerin, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 29 parts lipid substances, 9.97 parts filler, 33 parts tobacco material, 2 parts glycerin, 1 part salt, 25 parts sweetener, and 0.03 parts flavorant.

Example 33

A smokeless tobacco composition suitable for use as a meltable smokeless tobacco product for oral use is provided in the following manner.

A tobacco material having tobacco particles with an average particle size of about 30 microns is provided. The tobacco material is dried in open atmosphere at about 54° C. to reduce the moisture content from about 50 percent to less than about 10 percent. Various dry ingredients are provided, which include a filler (erythritol), a salt (sodium chloride), a sweetener (sucrose), and a flavorant (vanillin). All dry ingredients, in powder form, as well the dried tobacco material, are added together and thoroughly mixed in a Hobart mixer with a paddle for about three minutes at about 120 rpm.

A lipid substance having a melting point of about 27° C. to about 34° C. is provided (available from Barry Callebaut CB302) and a second lipid having a melting point of about 36° C. to 39° C. (available as CEBES 27-70 from AarhusKarlshamn USA Inc.). The lipid substance CB302 is de-odorized natural cocoa butter and CEBES 27-70 is hydrogenated palm kernel oil.

The lipid substance is melted in a mixing vessel. While maintaining heat to the mixing vessel having the melted lipid substance, a small amount of glycerin is added as a processing aid. Following the glycerin, the mixed dry formulation is added while mixing occurs, thereby creating a flowable slurry of smokeless tobacco composition having a moisture content of less than about 10 percent. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 29 parts lipid substances, 9.97 parts filler, 33 parts tobacco material, 2 parts glycerin, 1 part salt, 25 parts sweetener, and 0.03 parts flavorant.

Example 34

A smokeless tobacco composition suitable for use as a meltable smokeless tobacco product for oral use is provided in the following manner.

A tobacco material in the form of an aqueous tobacco extract (extract of a tobacco mixture comprising 75% by weight flue-cured tobacco and 25% by weight burley tobacco) is heat-treated in the presence of lysine and spray-dried. Various dry ingredients are provided, which include a filler (isomalt), a salt (sodium chloride), a sweetener (sucralose), and two flavorants (vanillin and mint). All dry ingredients, in powder form, as well the spray-dried tobacco material, are added together and thoroughly mixed in a Hobart mixer with a paddle for about three minutes at about 120 rpm.

A lipid substance having a melting point of about 38° C. to about 42° C. is provided (available as 108-24-B from AarhusKarlshamn USA Inc.). The lipid substance is a non-hydrogenated lauric coating fat containing palm kernel oil and palm oil.

The lipid substance is melted in a mixing vessel using a microwave. The melted lipid is slowly added to the dry blend while stirring. While maintaining heat to the mixing vessel, addition of the entire melted lipid component creates a flowable slurry of smokeless tobacco composition. The slurry is deposited in a mold to achieve about 1 gram weight per piece of smokeless tobacco product. The slurry is allowed to harden by ambient air drying for about 45 minutes, after which the individual pieces of smokeless tobacco product are removed from the mold. The mixture of the smokeless tobacco composition is about 40 parts lipid substance, 56 parts filler, 2 parts tobacco extract, 0.5 parts salt, 0.45 parts sweetener, and 1.05 parts flavorant.

Example 35

A smokeless tobacco composition suitable for use as a meltable smokeless tobacco product for oral use is provided in the following manner. A composition is prepared as described in Example 34, except the heat-treated tobacco extract is first mixed with an extender component selected from maltodextrin, cyclodextrin, and gum arabic prior to spray-drying. The amount of extender added to the liquid extract is the amount sufficient to raise the solids content of the liquid extract to about 20% by weight. The resulting mixture is spray-dried to form a particulate composition with greater density and improved flowability, which enhances the mixing properties of the powder material. The final spray-dried powder has a weight ratio of tobacco extract to extender ingredient of about 3:1. The spray-dried powder is used in place of the tobacco extract component as described in Example 34, although the amount of spray-dried material is increased such that the spray-dried tobacco extract composition is present in an amount of about 2.5 parts by weight in the final smokeless tobacco composition, and the lipid component is reduced to 39.5 parts by weight.

That which is claimed:

1. A meltable composition configured for insertion into the mouth of a user and capable of liquefying in the mouth, the meltable composition comprising a tobacco extract, a botanical component, at least 35 dry weight percent of a lipid having a melting point of 29° C. to 49° C., and at least about 50 dry weight percent of at least one filler comprising a sugar alcohol.

2. The meltable composition of claim 1, wherein the botanical component is selected from the group consisting of tea particulates, coffee particulates, herbal particulates, spice particulates and combinations thereof.

3. The meltable composition of claim 1, wherein the tobacco extract is an aqueous tobacco extract in spray-dried or freeze-dried particulate form.

4. The meltable composition of claim 1, wherein the tobacco extract is in the form of a particulate mixture of spray-dried or freeze-dried tobacco extract particles and a second spray-dried or freeze-dried particulate material.

5. The meltable composition of claim 4, wherein the second particulate material is a filler or binder material selected from the group consisting of maltodextrin, cyclodextrin, and natural gums.

6. The meltable composition of claim 1, wherein the lipid has a melting point of 36° C. to 45° C.

7. The meltable composition of claim 1, wherein the lipid has a melting point of 38° C. to 41° C.

8. The meltable composition of claim 1, wherein the lipid comprises a blend of palm kernel oil and palm oil.

9. The meltable composition of claim 1, wherein the sugar alcohol is isomalt.

10. The meltable composition of claim 1, further comprising lecithin.

* * * * *